(12) United States Patent
Ohshika et al.

(10) Patent No.: US 10,485,899 B2
(45) Date of Patent: Nov. 26, 2019

(54) POLYTETRAFLUOROETHYLENE TUBE

(71) Applicant: JUNKOSHA INC., Kasama-shi, Ibaraki (JP)

(72) Inventors: Nozomi Ohshika, Kasama (JP); Syunsuke Munakata, Kasama (JP)

(73) Assignee: JUNKOSHA INC., Kasama-Shi (JP)

( * ) Notice: Subject to any disclaimer, the term of this patent is extended or adjusted under 35 U.S.C. 154(b) by 0 days.

(21) Appl. No.: 16/250,439

(22) Filed: Jan. 17, 2019

(65) Prior Publication Data

US 2019/0143003 A1 May 16, 2019

Related U.S. Application Data

(63) Continuation of application No. 15/645,358, filed on Jul. 10, 2017, now Pat. No. 10,183,098, which is a (Continued)

(30) Foreign Application Priority Data

| Mar. 20, 2016 | (JP) | 2016-056365 |
| Mar. 29, 2016 | (JP) | 2016-066946 |
| Sep. 5, 2016 | (JP) | 2016-172416 |
| Mar. 3, 2017 | (JP) | 2017-041101 |

(51) Int. Cl.
| B29C 55/00 | (2006.01) |
| A61L 29/04 | (2006.01) |
| B29C 48/00 | (2019.01) |
| B29C 48/92 | (2019.01) |
| B29C 48/09 | (2019.01) |

(Continued)

(52) U.S. Cl.
CPC ........ *A61L 29/041* (2013.01); *B29C 48/0018* (2019.02); *B29C 48/022* (2019.02); *B29C 48/09* (2019.02); *B29C 48/92* (2019.02); *A61M 25/0009* (2013.01); *B29K 2027/18* (2013.01); *B29L 2023/00* (2013.01); *C08F 114/26* (2013.01)

(58) Field of Classification Search
CPC ... A61L 29/041; F16L 9/127; Y10T 428/1393
USPC .................................. 428/34.1, 35.7, 36.91
See application file for complete search history.

(56) References Cited

U.S. PATENT DOCUMENTS

| 4,225,547 A | 9/1980 | Okita |
| 5,122,592 A | 6/1992 | Khanna et al. |

(Continued)

FOREIGN PATENT DOCUMENTS

| JP | 07-102413 | 4/1995 |
| JP | 2000-316977 | 11/2000 |

(Continued)

OTHER PUBLICATIONS

PCT/ISA/237 (Partial English Translation included) and PCT/ISA/210 in PCT/JP2017/009559 mailed on Jun. 13, 2017 9 pages.

*Primary Examiner* — Ellen S Wood
(74) *Attorney, Agent, or Firm* — Rankin, Hill & Clark LLP

(57) ABSTRACT

A polytetrafluoroethylene tube is provided and has a thickness of 0.1 mm or less, a tensile elongation at break of 350% or more, and a melting energy of 0.6 J/g or more which is calculated from an endothermic peak at 370° C.±5° C. in a procedure of increasing a temperature in differential scanning calorimetry (DSC).

18 Claims, 1 Drawing Sheet

Related U.S. Application Data continuation of application No. PCT/JP2017/009559, filed on Mar. 9, 2017.

(51) Int. Cl.
  *B29K 27/18* (2006.01)
  *B29L 23/00* (2006.01)
  *C08F 114/26* (2006.01)
  *A61M 25/00* (2006.01)

(56) References Cited

U.S. PATENT DOCUMENTS

| | | | |
|---|---|---|---|
| 6,716,239 B2* | 4/2004 | Sowinski | A61F 2/06 600/36 |
| 2004/0213936 A1* | 10/2004 | Yoshimoto | A61L 29/041 428/36.91 |
| 2008/0020159 A1 | 1/2008 | Taira et al. | |
| 2009/0097890 A1 | 4/2009 | Oyama | |
| 2009/0234329 A1 | 9/2009 | Inamoto et al. | |
| 2011/0180955 A1 | 7/2011 | Inamoto et al. | |
| 2016/0289361 A1 | 10/2016 | Yamanaka et al. | |

FOREIGN PATENT DOCUMENTS

| | | |
|---|---|---|
| JP | 2004-340364 | 12/2004 |
| JP | 2007-185931 | 7/2007 |
| JP | 2008-223019 | 9/2008 |
| JP | 2009-001595 | 1/2009 |
| JP | 2010-155361 | 7/2010 |
| JP | 2010-226936 | 10/2010 |
| JP | 2010-280915 | 12/2010 |
| JP | 2013-176583 | 9/2013 |
| JP | 2015-127411 | 7/2015 |
| JP | 2015-178614 | 10/2015 |
| WO | 1995005132 | 2/1995 |

* cited by examiner

POLYTETRAFLUOROETHYLENE TUBE

CROSS-REFERENCE TO RELATED APPLICATION

This application is a continuation of International Application No. PCT/JP2017/009559 filed on Mar. 9, 2017, which is based on and claims priority from Japanese Patent Application Nos. 2016-056365, 2016-066946, 2016-172416, and 2017-041101, filed on Mar. 20, 2016, Mar. 29, 2016, Sep. 5, 2016, and Mar. 3, 2017, respectively, the entire contents of which are hereby incorporated by reference.

BACKGROUND OF THE INVENTION

Technical Field

The present invention relates to a fluororesin tube, and particularly, to a tube of polytetrafluoroethylene (referred to as "PTFE" below) as a material of the tube, having a thin thickness.

Background Art

A PTFE tube is suitably used in a material and the like of a medical catheter because of excellent characteristics such as chemical resistance, non-adhesiveness, and low friction. In an endovascular surgery, a catheter is inserted into a blood vessel and a lesion site in a blood vessel is removed, treated, or the like. Because a burden of a patient is small, such an endovascular surgery becomes the mainstream. It is necessary that a catheter used for such a purpose is percutaneously inserted toward the inside of a body, and a tip end of the tube is caused to reach a lesion site via a blood vessel. In addition, the catheter requires, for example, straightness which represents straightly traveling in a blood vessel and operation transmissibility which represents transmission of an operation of a practitioner who performs treatment. In order to satisfy the demand, the catheter is configured by stacking layers which have different characteristics. The inner diameter of the catheter is preferably as large as possible, because it is necessary that, for example, a jig is inserted or a chemical liquid is injected into the catheter. In addition, the outer diameter of the catheter is preferably small in order to reduce the burden on a patient. Thus, each of the layers constituting the catheter is required to be as thin as possible.

As one method of manufacturing a catheter tube, there is a method in which a core wire such as a copper wire is coated with PTFE, an exterior resin layer is formed on the resultant of the coating, then the core wire is pulled out, and thereby a catheter tube is obtained (for example, see Patent Document 1). As a method of coating a core wire with PTFE, there are a method (referred to as "a dipping method" below) of coating a core wire with a PTFE dispersion and sintering the resultant of the coating, and a method of performing direct paste extrusion forming on the core wire. In addition, there is a method of performing coating by covering a core wire with a PTFE tube. At this time, the PTFE tube is extended in a state where the core wire is inserted into the PTFE tube, the diameter thereof is reduced, and thus the PTFE tube adheres to the core wire. Thus, the tube requires an elongation for performing extension and a tensile strength for withstanding extension.

Since PTFE has a very large melt viscosity, a PTFE tube is generally formed by not melt extrusion forming but paste extrusion forming (for example, see Patent Document 2). However, in the paste extrusion forming, it is difficult to form a tube having a thin thickness. In a case of forming a PTFE tube having a thin thickness, the dipping method is much used (for example, see Patent Document 3). However, a tube formed by the dipping method has a problem of weak tensile strength.

For example, Patent Document 4 discloses a method in which the paste extrusion forming is performed, and then the tube is extended in a longitudinal direction so as to reduce the thickness, in order to obtain a tube which has a thin thickness and a large tensile strength.

CITATION LIST

Patent Document 1: JP-A-2013-176583
Patent Document 2: JP-A-2010-226936
Patent Document 3: JP-A-2000-316977
Patent Document 4: JP-A-2004-340364

SUMMARY

In the technique disclosed in Patent Document 4, since extension is performed for reducing the thickness, the tensile strength of a PTFE tube is large, but the tensile elongation is reduced. As described above, it is difficult that a PTFE tube having a thin thickness obtains both the tensile elongation and the tensile strength. Accordingly, an object of the present invention is to provide a PTFE tube which is a thin PTFE tube and has a large tensile strength, while having a large tensile elongation at break.

The object of the present invention is achieved by a polytetrafluoroethylene tube having a thickness of 0.1 mm or less, a tensile elongation at break of 350% or more, and a melting energy of 0.6 J/g or more which is calculated from an endothermic peak at 370° C.±5° C. in a procedure of increasing a temperature in differential scanning calorimetry (DSC).

The object of the present invention is achieved by a polytetrafluoroethylene tube having a thickness of 0.1 mm or less, a tensile elongation at break of 450% or more, and a melting energy of 0.6 J/g or more which is calculated from an endothermic peak at 370° C.±5° C. in a procedure of increasing a temperature in differential scanning calorimetry (DSC).

Further, the object of the present invention is achieved by a polytetrafluoroethylene tube in which a tensile strength at a tube displacement amount of 10 mm when being measured at a distance of 50 mm between chucks is 50 N/mm$^2$ or more.

A tube according to the present invention has a large tensile strength, while having a large tensile elongation at break, and thus it can be suitably used, for example, in a case where a PTFE tube is deformed by extension to be used for coating a core material.

REFERENCE SIGN LIST IN DRAWINGS

1: Endothermic Peak at 370° C.±5° C.

DETAILED DESCRIPTION OF THE INVENTION

Hereinafter, a PTFE tube according to an embodiment of the present invention will be described in detail. The embodiment which will be described below does not limit the inventions relating to the scope of claims and all combinations of features described in the embodiment are not essential for establishing the present invention.

In the embodiment of the present invention, the thickness of a PTFE tube is 0.1 mm or less. Specifically, the thickness thereof is 0.005 to 0.1 mm, preferably 0.01 to 0.08 mm, and further preferably 0.01 to 0.05 mm. Alternatively, a PTFE tube has a thickness of 5% or less of the outer diameter thereof, and preferably, 4% or less of the outer diameter thereof. When the PTFE tube is used as a part of a layer of a catheter, if the thickness is thin, it is possible to reduce the diameter of the catheter without disturbing the function of the catheter.

The PTFE tube in the present invention has a tensile elongation at break of 350% or more. More preferably, the PTFE tube has a tensile elongation at break of 450% or more. The tensile elongation at break means an elongation of a tube until the tube is broken, when being measured at a pulling rate of 50 mm/min, under the surrounding environment of 23° C.±2° C.

The PTFE tube in the present invention has a melting energy of 0.6 J/g or more. The melting energy is calculated from an endothermic peak at 370° C.±5° C. in a procedure of increasing a temperature in differential scanning calorimetry (DSC). If the DSC measurement is performed on a sample obtained by crushing the PTFE tube in the present invention, endothermic peaks by melting crystals are observed. Due to variety of crystal structures, two peaks on a low temperature side and on a high temperature side are observed.

Figure 1:
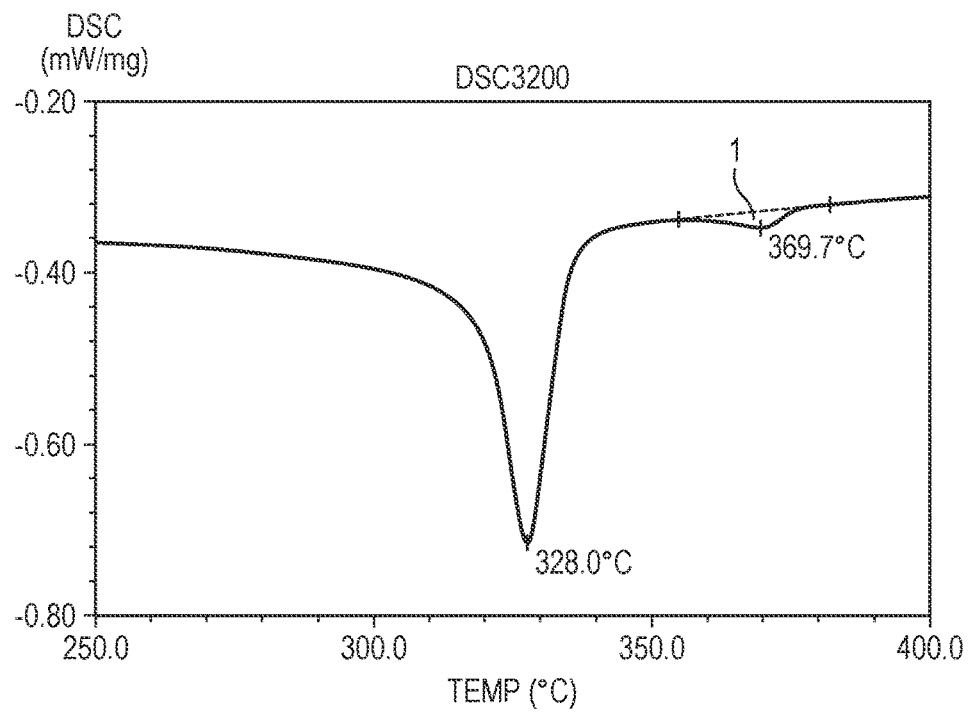
FIG. 1 is a DSC curve of a PTFE tube according to the present invention.

FIG. 1 illustrates an example of a DSC curve of a tube in an embodiment of the present invention. In a case of the PTFE tube in the present invention, in the procedure of increasing a temperature at a temperature rising rate of 10° C./min, a large endothermic peak is observed in the vicinity of 327° C. and a small endothermic peak is observed in the vicinity of 370° C. The melting energy can be calculated from an area of the endothermic peaks. It is considered that the endothermic peak at the vicinity of 327° C. is caused by melting a folded chain crystal and the endothermic peak at the vicinity of 370° C. is caused by melting a stretched chain crystal. In a case where extension is performed after the tube is formed, the endothermic peak 1 at 370° C.±5° C. tends to be large. In order to increase the tensile strength of the tube, it is effective that molecules of a resin forming the tube are arranged in an axial direction of the tube in which the main chain is stretched. Entangled fibrils are paralleled and arranged in an extrusion flow direction, that is, the axial direction of the tube, when the fibrils are discharged from an outlet of a mold. It is considered that the arranged fibrils show an endothermic peak in the vicinity of 370° C., as the stretched chain crystal. The PTFE tube in the present invention forms a tube in which the melting energy of the endothermic peak 1 is large while extension of the tube after formation is suppressed to be 5% or less.

The tube after formation is not extended, and thus a tube having a large tensile elongation at break is obtained. In a case where, for example, the PTFE tube is extended to be used for coating a core material, it is desirable that the tube has a tensile strength of 50 N/mm² or more when a tube displacement amount when being measured at a distance of 50 mm between chucks is 10 mm (hereinafter referred to as "a tube displacement amount"), or the tube has a tensile strength of 70 N/mm² or more when the tube displacement amount is 20 mm. When the tube has a melting energy of 0.6 J/g or more at 370° C.±5° C., it is possible to obtain a tube having a tensile strength f 50 N/mm² or more when the tube displacement amount is 10 mm, or a tube having a tensile strength of 70 N/mm² or more when the tube displacement amount is 20 mm.

The tensile strength referred in the present invention indicates a tensile strength when a tube displacement amount (extended amount) at an initial time of pulling is 10 mm or 20 mm in a tensile test. In the above-described method of coating a core wire with a PTFE tube, the tensile strength for a period until the PTFE tube is extended and adheres to the core wire is required. Thus, the tensile strength when the displacement amount of the tube is 10 mm or 20 mm is used as a criterion for evaluating the tensile strength for that period.

Hereinafter, a configuration of the PTFE tube in the embodiment of the present invention will be described in detail.

There are two types of PTFE powder for forming: fine powder and molding powder. In the embodiment of the present invention, fine powder obtained by emulsion polymerization is used. The fine powder has properties of deforming with fibrillation if a shearing force is applied. In paste extrusion forming, these properties are used. The paste extrusion forming is a method as follows. The fine powder is mixed with an organic solvent which is generally referred to as an auxiliary agent (lubricant) and the mixture is compressed, thereby creating a preformed body. The preformed body is extruded at a forming temperature of 70° C. or lower by using an extrusion machine, so as to perform formation. The paste extrusion forming is used for creating a film, a tube, an electric-wire coating material, and the like.

PTFE used in the embodiment of the present invention may be a homopolymer of tetrafluoroethylene (hereinafter referred to as "TFE") or may be modified PTFE. The modified PTFE is obtained by polymerizing TFE and a small amount of monomers other than TFE. Examples of the small amount of monomers other than TFE include chlorotrifluoroethylene (CTFE), hexafluoropropylene (HFP), and perfluoroalkyl vinyl ether (PPVE).

It is possible to change heat resistance, abrasion resistance, bending resistance, and the like of a molded object by using modified PTFE.

The PTFE fine powder is generally powder in which primary particles having an average particle diameter of 0.2 to 0.5 μm are aggregated, and thereby secondary particles having an average particle diameter of 400 to 700 μm are formed. In the embodiment of the present invention, fine powder having an average secondary particle diameter of 400 to 600 μm is used.

The auxiliary agent is added to PTFE fine powder, and thus allows the PTFE fine powder to be made to be a paste and allows extrusion to be performed. Thus, an organic solvent having high lubricity is preferably used as the auxiliary agent used in the embodiment of the present invention. After the auxiliary agent is added to the PTFE fine powder, a tube is formed in an extrusion machine by using a mold. If the auxiliary agent is volatilized during the forming, it is difficult to perform stable forming, which is not preferable. It is preferable that the auxiliary agent used in the embodiment of the present invention has an initial boiling point (IBP) of 150° C. or higher. After the tube is formed by using the PTFE fine powder and the auxiliary agent, the auxiliary agent is removed by volatilizing the auxiliary agent before the tube is sintered. At this time, the IBP of the auxiliary agent is preferably 250° C. or lower, so as to enable the auxiliary agent to be reliably removed. A petroleum solvent is particularly preferably used as an organic solvent which has high lubricity and an IBP of 150° C. to 250° C.

An auxiliary agent in which a difference between the interfacial tension of PTFE and the interfacial tension of the auxiliary agent is small is used as the auxiliary agent used in paste extrusion in the related art (see Patent Document 1). However, it is preferable that the auxiliary agent used in the embodiment of the present invention has an interfacial tension which is more than 18.5 mN/m of the interfacial tension of PTFE by 4 mN/m or more. It is considered that, since the interfacial tension of the auxiliary agent is high, the auxiliary agent is difficult to move between PTFE particles and is easy to stay on the surface of the particles. In PTFE paste extrusion, when particles slide in the mode at a time of extrusion, the surfaces of the particles are subjected to fibrillating and the fibrils are entangled. Thus, deformation is difficult and extrusion pressure is increased. At this time, since the auxiliary agent is present between the particles, entanglement of PTFE particles is suppressed and the increase of the extrusion pressure is suppressed.

In order to set the thickness of the PTFE tube to be 0.1 mm or less or in order to obtain a tube having a thickness of 5% or less of the outer diameter, forming is performed under conditions of a very narrow flow passage in which resin in the mold flows and high Reduction Ratio (hereinafter referred to as "RR"). In the condition of high RR, a shearing force generated between the PTFE particle and the inner wall of the mold and between the PTFE particles becomes large. If shear stress which is rapidly increased is applied to the PTFE particles, most of the PTFE particles are subjected to fibrillating in one lump and the extrusion pressure is increased. The inside of a die is in a turbulent state and over-shearing occurs. In a tube which has been formed in an over-shearing state, the surface is rough, distortion occurs in the tube, or defects and the like occur. Further, if the extrusion pressure is too high and exceeds a capability range of the extrusion machine, extrusion is not possible.

In the embodiment of the present invention, the auxiliary agent stays between the PTFE particles, and thus an effect of reducing a shearing force between the PTFE particles and between the PTFE particle and the inner wall of the mold is high, and an occurrence in which PTFE is too fast subjected to fibrillating and an increase of the extrusion pressure can be suppressed. Therefore, it is possible to obtain a tube in which defects of which the number is small inside and outside the molded object. In addition, a tube having a large tensile strength is obtained, while having a tensile elongation at break of 350% or more. It is more preferable that tensile elongation at break is 450% or more.

The tube in the embodiment of the present invention may include a filler or other resins. Examples of the filler include carbon, a metal oxide such as alumina, a resin filler, and the like. One or plural types of the fillers may be mixed in PTFE and the mixture may be used.

A manufacturing method of the tube in the embodiment of the present invention will be described below.

(Forming of Preformed Body)

PTFE and an auxiliary agent are mixed in a tumbler or the like. As described above, an auxiliary agent having an interfacial tension which is higher than the interfacial tension of PTFE by 4 mN/m or greater is used. The auxiliary agent preferably has an IBP of 150° C. to 250° C. The mixture of the PTFE and the auxiliary agent is pressed and formed, thereby forming a preformed body.

(Extrusion Forming)

The preformed body is set in an extrusion machine, and is formed to have a tube shape by using a mold. Since the tube according to the embodiment of the present invention has a thickness of 0.1 mm or less, a very high shear stress is applied when the preformed body passes through a taper portion of the mold. Here, in the embodiment of the present invention, an auxiliary agent having an interfacial tension which is higher than the interfacial tension of PTFE by 4 mN/m or more is used. Thus, the auxiliary agent stays between PTFE particles and lubricity between the PTFE particles and between the PTFE particle and the inner wall of the mold is high. Thus, it is possible to suppress an occurrence of rapid fibrillation of PTFE particles. Accordingly, the increase of the extrusion pressure is suppressed.

A temperature of a die for paste extrusion in the related art is known to be 70° C. or less (for example, see Patent Document 1). However, in the embodiment of the present invention, the temperature of a die is preferably set to be 100° C. to 200° C. and more preferably set to be 130° C. to 200° C. Since the temperature of the die is set to be high, fibrillation is accelerated on the surface of the PTFE particles and the formed fibril is discharged from the outlet of the mold, in a state of being entangled. Excessively rapid fibrillation of PTFE is suppressed and fibrillation on the surface of PTFE particle and entanglement of fibrils are accelerated, and thus the tube after sintering has a large tensile strength while having a tensile elongation at break of 450% or more. In particularly, the entanglement of fibrils is accelerated, and thus a tube having a large tensile strength at an initial time of displacement.

(Drying Process)

PTFE formed to have a tube shape is heated at a temperature which is equal to or lower than a melting point of PTFE, so as to volatilize the auxiliary agent. When PTFE is sintered in a post-process, it is not preferable that the auxiliary agent remains. Thus, the auxiliary agent is sufficiently volatilized. Since the auxiliary agent having an IBP of 150° C. to 250° C. is used in the tube in the embodiment of the present invention, in a drying process, the auxiliary agent can be sufficiently removed. In the drying process, an occurrence of a situation in which tension is applied to the tube and the tube is extended is suppressed. Thus, for example, the balance of the tube between sending and drawing is adjusted. The adjustment is preferably performed such that the extension of the tube is within 5%.

(Sintering of Tube)

Sintering is performed by heating the dried PTFE tube to a temperature which is equal to or higher than the melting point of PTFE. Generally, the tube is heated at substantially 400° C. Since the tube is heated at the temperature which is equal to or higher than the melting point, PTFE particles are adhered to each other.

The invention will be more specifically described based on the following examples. The following examples are just only examples and the contents of the present invention are not limited to the following examples.

EXAMPLES

<Tensile Elongation at Break and Tensile Strength>

A tensile test was performed under an environment of 23° C.±2° C. by using AUTOGRAPH AGS-1 kN X type which is manufactured by Shimadzu Corporation. The tensile test was performed in conditions of a distance of 50 mm between chucks and a chuck speed of 50 mm/min.

A stress value when a tube set in the chucks was extended in a longitudinal direction by 10 mm and a stress value when the tube is extended in the longitudinal direction by 20 mm were measured as tensile strengths. The test was performed until the tube was broken, and the tube extension when the tube was broken was set to be a tensile elongation at break.

<Differential Scanning Calorimetry>

The measurement was performed by using DSC3200SA manufactured by NETZSCH JAPAN Corporation, in a manner that a temperature was increased from room temperature at a temperature rising rate of 10° C./min. The melting energy was calculated from an area obtained by the endothermic peaks of 370° C.±5° C. in the obtained endothermic curve of DSC.

Example 1

18 parts by mass of an auxiliary agent (ISOPER H manufactured by Exxon Mobil Corporation) with respect to 100 parts by mass of PTFE fine powder (POLYFLON PTFE F-208 manufactured by Daikin Industries, Ltd.) were put into a container and mixed. Lumps in the mixture were removed by a sieve of #10 and the resultant was put into a preforming machine, and thereby a preformed body was produced. As an extrusion forming machine used in extrusion forming of a tube, a machine in which a cylinder diameter was 20 mm and a mandrel diameter was 10 mm was used. An inner diameter of a die was set to 0.77 mm, a core pin was set to 0.66 mm, and a temperature of the die was set to 120° C. The preformed body was put into the extrusion forming machine. Extrusion was performed at a ram speed of 3 mm/min, thereby a tube shape was formed. The formed tube was dried and burned by passing through a first drying furnace (set to be 150° C.), a second drying furnace (set to be 220° C.), and a firing furnace (set to be 430° C.). When the tube was dried and burned, the speed of a drawing machine was adjusted so as not to apply an extra tension to the tube. The finished tube was 0.49 mm in inner diameter, 0.566 mm in outer diameter, and 0.038 mm in thickness. The obtained tube was cut to be 100 mm, and a tensile test was performed. Thus, the tensile strength and the tensile elongation at break were measured. Samples were taken from the obtained tubes in accordance with the number or sites of the tubes. The taken samples were ground and mixed, thereby obtaining a test piece. The DSC measurement was performed on the test piece and the melting energy was calculated from a peak area. Table 1 shows results.

Example 2

A tube was produced in a manner similar to that in Example 1 except that the temperature of an extrusion die was set to 140° C. The tensile test and the DSC measurement were performed on the tube.

Example 3

A tube was produced in a manner similar to that in Example 1 except that an auxiliary agent mixed in PTFE fine powder was set to be ISOPER M manufactured by Exxon Mobil Corporation. The tensile test and the DSC measurement were performed on the tube.

Example 4

A tube was produced in a manner similar to that in Example 3 except that PTFE640J manufactured by Du Pont-Mitsui Fluorochemicals Co., Ltd was used as the PTFE fine powder. The tensile test and the DSC measurement were performed on the tube.

Example 5

PTFE F-201 manufactured by Daikin Industries, Ltd. was used as the PTFE fine powder and ISOPER L manufactured by Exxon Mobil Corporation was used as the auxiliary agent. A mixing ratio and a mixing method were similar to those in Example 1. A tube was produced in a manner similar to that in Example 1 except that a mold in which an inner diameter of a die was 0.72 mm and a core pin was 0.66 mm was used as the extrusion mold. The tensile test and the DSC measurement were performed on the tube.

Example 6

PTFE640J manufactured by Du Pont-Mitsui Fluorochemicals Co., Ltd was used as the PTFE fine powder and ISOPER G manufactured by Exxon Mobil Corporation was used as the auxiliary agent. A mixing ratio and a mixing method were similar to those in Example 1. A tube was created in a manner similar to that in Example 1 except that a mold in which an inner diameter of a die was 2.61 mm and a core pin was 2.40 mm was used as the extrusion mold. The tensile test and the DSC measurement were performed on the tube.

Comparative Example 1

A tube was produced in a manner similar to that in Example 1 except that the temperature of the extrusion die was set to 80° C. The tensile test and DSC measurement were performed on the tube.

Comparative Example 2

Extrusion forming was performed in a manner similar to that in Example 1 except that ISOPER E manufactured by Exxon Mobil Corporation was used as the auxiliary agent. Since extrusion pressure was higher than an upper limit of the extrusion machine (mold), extrusion was suspended.

Table 1 shows results in Examples, Comparative Examples 1 and 2.

TABLE 1

|  |  | Example 1 | Example 2 | Example 3 | Example 4 | Example 5 | Example 6 | Comparative Example 1 | Comparative Example 2 |
|---|---|---|---|---|---|---|---|---|---|
| Tube inner diameter | mm | 0.49 | 0.49 | 0.49 | 0.49 | 0.475 | 1.72 | 0.49 | 0.49 |
| Tube thickness | mm | 0.038 | 0.038 | 0.038 | 0.038 | 0.028 | 0.053 | 0.038 | 0.038 |
| Thickness % for outer diameter |  | 6.7 | 6.7 | 6.7 | 6.7 | 5.4 | 2.9 | 6.7 | 6.7 |
| Auxiliary agent interfacial tension | mN/m | 23 | 23 | 25 | 25 | 23 | 24 | 23 | 21 |
| Extrusion die temperature | ° C. | 120 | 140 | 120 | 120 | 120 | 120 | 80 | 120 |
| Extrusion pressure | kN | 21.9 | 23 | 19.5 | 22.7 | 28.1 | 18.4 | 17.8 | 35< |

TABLE 1-continued

|  |  | Example 1 | Example 2 | Example 3 | Example 4 | Example 5 | Example 6 | Comparative Example 1 | Comparative Example 2 |
|---|---|---|---|---|---|---|---|---|---|
| Melting energy at 370° C. ± 5° C. | J/g | 1.22 | 0.945 | 0.699 | 0.824 | 1.34 | 0.705 | 0.19 | — |
| Tensile strength when the tube displacement amount is 10 mm | N/mm$^2$ | 76.6 | 75.3 | 70.0 | 70.4 | 93.0 | 62.0 | 17.0 | — |
| Tensile elongation at break | % | 654 | 544 | 506 | 520 | 460 | 583 | 580 | — |

Figure 2:
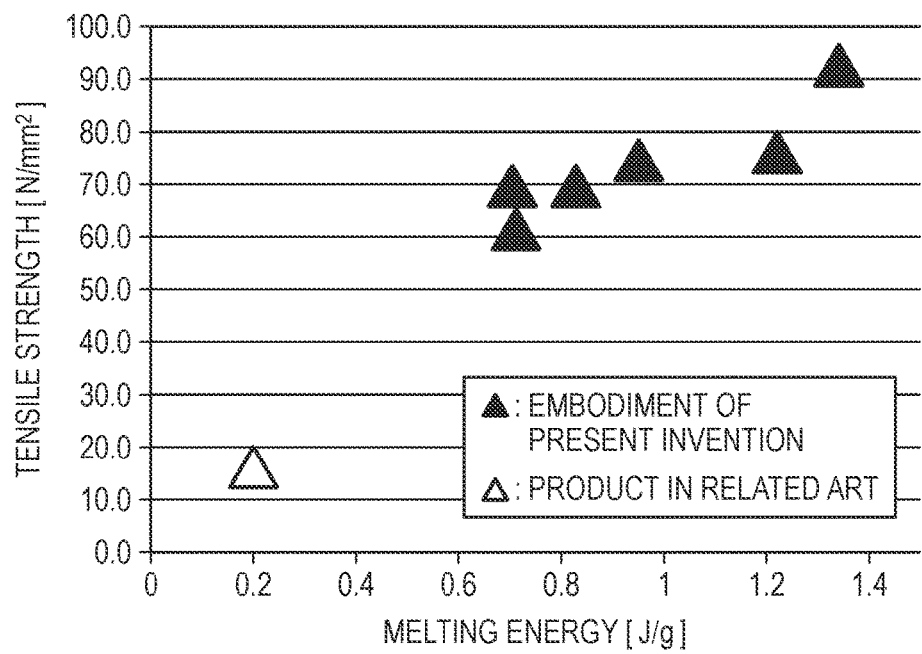
FIG. 2 is a diagram illustrating a relationship between melting energy calculated from an endothermic peak at 370° C.±5° C., and tube tensile strength in the PTFE tube of the present invention.

FIG. 2 illustrates a relationship between the melting energy calculated from endothermic peaks at 370° C.±5° C. and the tensile strength regarding the PTFE tubes of the examples and the comparative examples in Table 1. If the melting energy is increased, a tendency of the tensile strength increasing is shown. In a case where, for example, the PTFE tube is extended to be used for coating a core material, it is desirable that the tensile strength when the tube displacement amount is 10 mm is 50 N/mm$^2$ or more, or the tensile strength when the tube displacement amount is 20 mm is 70 N/mm$^2$ or more. In the example in which the melting energy was 0.6 J/g or more, a tube in which the tensile elongation at break was 450% or more and the tensile strength when the tube displacement amount was 10 mm was 50 N/mm$^2$ or more was obtained. Regarding the tube in Comparative Example 1 in which the temperature of the die was set to 80° C. and a manufacturing method in the related art was applied, the tensile elongation at break was 580% or more, that is, large. However, the tensile strength was only 17.8 N/mm$^2$. Thus, if, for example, the PTFE tube was extended to be used for coating a core material, a PTFE tube which practically withstood the stress was not obtained.

Comparative Example 3

A preformed body was prepared in a manner similar to that in Example 1 except that ISOPER E manufactured by Exxon Mobil Corporation was used as the auxiliary agent. The tensile test and the DSC measurement were performed on the tube. In Comparative Example 2, since extrusion pressure exceeded a usable range of the extrusion machine (mold) which had been used, extrusion was suspended. Thus, the shape was changed to be a shape of a mandrel so as to withstand the extrusion pressure and forming was performed. Extrusion forming was performed in a manner similar to that in Example 1 except for the shape of the mandrel.

Comparative Example 4

A preformed body was created in a manner similar to that in Example 1. The preformed body was put into an extrusion forming machine, and a PTFE layer was extruded on an annealed copper wire having an outer diameter of 0.495 mm. The extrusion forming machine in which a cylinder diameter was 20 mm, a mandrel diameter was 10 mm, an inner diameter of the die was 0.6 mm, and the temperature of the die was 120° C. had been used. A ram speed was set to be 3 mm/min. The resultant was dried and burned by passing through a first drying furnace (set to be 150° C.), a second drying furnace (set to be 220° C.), and a firing furnace (set to be 430° C.). After burning, the annealed copper wire extended and thus pulled out from the PTFE layer. Thus, a tube was produced. The finished tube was 0.49 mm in inner diameter, 0.566 mm in outer diameter, and 0.038 mm in thickness. The tensile test and the DSC measurement were performed on the obtained tube in a manner similar to those in Example 1.

Comparative Example 5

An annealed copper wire having an outer diameter of 0.495 mm was coated with an aqueous dispersion (POLYFLON PTFE D-1 manufactured by Daikin Industries, Ltd.). Then, drying and burning were performed. The above process repeated until the outer diameter reached 0.566 mm, and thereby a PTFE layer was formed. The annealed copper wire was extended and thus pulled out from the PTFE layer. Thus, a tube was produced. The finished tube was 0.49 mm in inner diameter, 0.566 mm in outer diameter, and 0.038 mm in thickness. The tensile test and the DSC measurement were performed on the obtained tube in a manner similar to those in Example 1.

Table 2 shows results in Comparative Examples 3 to 5.

TABLE 2

|  |  | Comparative Example 3 | Comparative Example 4 | Comparative Example 5 |
|---|---|---|---|---|
| Tube inner diameter | mm | 0.49 | 0.49 | 0.49 |
| Tube thickness | mm | 0.038 | 0.038 | 0.038 |
| Thickness % for outer diameter |  | 6.7 | 6.7 | 6.7 |
| Auxiliary agent interfacial tension | mN/m | 21 | 23 | — |
| Extrusion die temperature | ° C. | 120 | 120 | — |
| Extrusion pressure | kN | 56.5 | 22.8 | — |
| Melting energy at 370° C. ± 5° C. | J/g | 0.29 | 0.39 | Detection impossible |
| Tensile strength when the tube displacement amount is 10 mm | N/mm$^2$ | 36.1 | 41.0 | 12.0 |
| Tensile elongation at break | % | 370 | 560 | 480 |

In Comparative Example 3, the tube in which a difference between the interfacial tension of the auxiliary agent and the interfacial tension of PTFE was only 2.5 mN/m and the tensile strength was small was obtained. It was considered that, since the extrusion pressure was increased too high, an over-shearing state occurred and a good molded object was not obtained. The tubes in Comparative Examples 4 and 5 are tubes which have been formed by the method in the related art and have a thin thickness. The tensile elongation at break was obtained, but a sufficient tensile strength was not obtained.

Example 7

PTFE640J manufactured by Du Pont-Mitsui Fluorochemicals Co., Ltd was used as the PTFE fine powder and ISOPER G manufactured by Exxon Mobil Corporation was used as the auxiliary agent. A mixing ratio and a mixing method were similar to those in Example 1. A tube which was 1.9 mm in inner diameter, 1.966 mm in outer diameter, and 0.033 mm in thickness was produced. The tensile test and the DSC measurement were performed.

Example 8

A tube was produced in a manner similar to that in Example 1 except that an auxiliary agent mixed in PTFE fine powder was set to be ISOPER G manufactured by Exxon Mobil Corporation. Regarding the size of the tube, the inner diameter was set to 2.3 mm, the outer diameter was set to 2.356 mm, and the thickness was set to 0.028 mm. The tensile test and the DSC measurement were performed.

Table 3 shows results in Examples 7 and 8.

TABLE 3

|  |  | Example 7 | Example 8 |
| --- | --- | --- | --- |
| Tube inner diameter | mm | 1.91 | 2.30 |
| Tube thickness | mm | 0.033 | 0.028 |
| Thickness % for outer diameter |  | 1.7 | 1.2 |
| Auxiliary agent interfacial tension | mN/m | 24 | 24 |
| Extrusion die temperature | ° C. | 120 | 140 |
| Extrusion pressure | kN | 18 | 19 |
| Melting energy at 370° C. ± 5° C. | J/g | 0.64 | 0.72 |
| Tensile strength when the tube displacement amount is 10 mm | N/mm$^2$ | 56.1 | 68.0 |
| Tensile elongation at break | % | 370 | 470 |

In Example 7, a tube in which the tensile elongation at break was 350% or more, the melting energy was 0.6 J/g or more, and the tensile strength when the tube displacement amount was 10 mm was 56.1 N/mm$^2$ was obtained. In Example 8, a tube in which the tensile elongation at break was 450% or more, the melting energy was 0.6 J/g or more, and the tensile strength when the tube displacement amount was 10 mm was 68.0 N/mm$^2$ was obtained.

INDUSTRIAL APPLICABILITY

According to the present invention, the tube can be particularly applied to a medical tube such a catheter.

What is claimed is:

1. A polytetrafluoroethylene tube having a thickness of 0.1 mm or less, a tensile strength at a tube displacement amount of 10 mm when being measured at a distance of 50 mm between chucks is 50 N/mm$^2$ or more, and a melting energy of 0.6 J/g or more which is calculated from an endothermic peak at about 370° C.±5° C. in a procedure of increasing a temperature in differential scanning calorimetry (DSC).

2. A polytetrafluoroethylene tube having a thickness of 5% or less of an outer diameter, a tensile strength at a tube displacement amount of 10 mm when being measured at a distance of 50 mm between chucks is 50 N/mm$^2$ or more, and a melting energy of 0.6 J/g or more which is calculated from an endothermic peak at about 370° C.±5° C. in a procedure of increasing a temperature in differential scanning calorimetry (DSC).

3. The polytetrafluoroethylene tube according to claim 1, wherein the tensile strength at the tube displacement amount of 10 mm when being measured at the distance of 50 mm between chucks is 70.4 N/mm$^2$ or more.

4. The polytetrafluoroethylene tube according to claim 1, wherein the thickness is 0.05 mm or less.

5. The polytetrafluoroethylene tube according to claim 4, wherein a tensile elongation at break is 350% or more.

6. The polytetrafluoroethylene tube according to claim 2, wherein the thickness is 0.05 mm or less.

7. The polytetrafluoroethylene tube according to claim 6, wherein a tensile elongation at break is 350% or more.

8. The polytetrafluoroethylene tube according to claim 4, wherein the tensile strength at the tube displacement amount of 10 mm when being measured at the distance of 50 mm between chucks is 70.4 N/mm$^2$ or more.

9. The polytetrafluoroethylene tube according to claim 8, wherein a tensile elongation at break is 350% or more.

10. The polytetrafluoroethylene tube according to claim 2, wherein the tensile strength at the tube displacement amount of 10 mm when being measured at the distance of 50 mm between chucks is 70.4 N/mm$^2$ or more.

11. The polytetrafluoroethylene tube according to claim 6, wherein the tensile strength at the tube displacement amount of 10 mm when being measured at the distance of 50 mm between chucks is 70.4 N/mm$^2$ or more.

12. The polytetrafluoroethylene tube according to claim 11, wherein a tensile elongation at break is 350% or more.

13. A polytetrafluoroethylene tube having a thickness of 0.1 mm or less, a tensile strength at a tube displacement amount of 10 mm when being measured at a distance of 50 mm between chucks is 50 N/mm$^2$ or more, and a melting energy of 0.824 J/g or more which is calculated from an endothermic peak at about 370° C.±5° C. in a procedure of increasing a temperature in differential scanning calorimetry (DSC).

14. The polytetrafluoroethylene tube according to claim 13, wherein the thickness is 0.05 mm or less.

15. The polytetrafluoroethylene tube according to claim 14, wherein a tensile elongation at break is 350% or more.

16. The polytetrafluoroethylene tube according to claim 13, wherein the tensile strength at the tube displacement amount of 10 mm when being measured at the distance of 50 mm between chucks is 70.4 N/mm$^2$ or more.

17. The polytetrafluoroethylene tube according to claim 14, wherein the tensile strength at the tube displacement amount of 10 mm when being measured at the distance of 50 mm between chucks is 70.4 N/mm$^2$ or more.

18. The polytetrafluoroethylene tube according to claim 17, wherein a tensile elongation at break is 350% or more.

* * * * *